United States Patent
Heaton et al.

(10) Patent No.: US 7,886,746 B2
(45) Date of Patent: *Feb. 15, 2011

(54) SURGICAL DRAPE AND SUCTION HEAD FOR WOUND TREATMENT

(75) Inventors: Keith Patrick Heaton, Poole (GB); Kenneth William Hunt, Wimbourne (GB)

(73) Assignee: KCI Licensing, Inc., San Antonio, TX (US)

( * ) Notice: Subject to any disclaimer, the term of this patent is extended or adjusted under 35 U.S.C. 154(b) by 684 days.

This patent is subject to a terminal disclaimer.

(21) Appl. No.: 11/545,321

(22) Filed: Oct. 10, 2006

(65) Prior Publication Data

US 2007/0032778 A1   Feb. 8, 2007

Related U.S. Application Data (63) Continuation of application No. 10/937,680, filed on Sep. 9, 2004, now Pat. No. 7,117,869, which is a continuation of application No. 10/366,227, filed on Feb. 13, 2003, now Pat. No. 6,814,079, which is a continuation of application No. 09/835,500, filed on Apr. 16, 2001, now Pat. No. 6,553,998, which is a continuation of application No. 09/350,581, filed on Jul. 9, 1999, now Pat. No. 6,345,623, which is a continuation of application No. PCT/GB98/02713, filed on Sep. 9, 1998.

(30) Foreign Application Priority Data

Sep. 12, 1997   (GB)   ................... 9719520.0

(51) Int. Cl.
    A61B 19/00   (2006.01)
(52) U.S. Cl. ........................ 128/897; 602/42
(58) Field of Classification Search ........ 128/897–898; 602/42–53
    See application file for complete search history.

(56) References Cited

U.S. PATENT DOCUMENTS

| | | | |
|---|---|---|---|
| 1,355,846 A | 10/1920 | Rannells |
| 2,305,289 A | 12/1942 | Coburg |
| 2,547,758 A | 4/1951 | Keeling |
| 2,632,443 A | 3/1953 | Lesher |

(Continued)

FOREIGN PATENT DOCUMENTS

AU   550575 A1   8/1982

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.

(Continued)

*Primary Examiner*—John P Lacyk (57) ABSTRACT

A wound therapy combination comprising a suction head and a surgical drape. The suction head comprises a planar flange portion and a tubular connector piece on a first face that communicates with an aperture extending to a second face. The second face is formed with projections that define flow channels for facilitating flow of liquids to the aperture.

21 Claims, 4 Drawing Sheets

U.S. PATENT DOCUMENTS

| | | |
|---|---|---|
| 2,682,873 A | 7/1954 | Evans et al. |
| 2,910,763 A | 11/1959 | Lauterbach |
| 2,969,057 A | 1/1961 | Simmons |
| 3,026,874 A | 3/1962 | Stevens |
| 3,066,672 A | 12/1962 | Crosby, Jr. et al. |
| 3,089,492 A | 5/1963 | Owens |
| 3,142,298 A | 7/1964 | Koski et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,250,882 A | 2/1981 | Adair |
| 4,256,109 A | 3/1981 | Nichols |
| 4,261,360 A | 4/1981 | Perez |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,342,745 A | 8/1982 | Mirkovitch |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,444,545 A | 4/1984 | Sanders et al. |
| 4,465,485 A | 8/1984 | Kashmer et al. |
| 4,468,219 A | 8/1984 | George et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,533,352 A | 8/1985 | Van Beek et al. |
| 4,534,356 A | 8/1985 | Papadakis |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,614,183 A | 9/1986 | McCracken et al. |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,795,435 A | 1/1989 | Steer |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,930,997 A | 6/1990 | Bennett |
| 4,941,882 A | 7/1990 | Ward et al. |
| 4,953,565 A | 9/1990 | Tachibana et al. |
| 4,969,880 A | 11/1990 | Zamierowski |
| 4,979,944 A | 12/1990 | Luzsicza |
| 4,985,019 A | 1/1991 | Michelson |
| 5,013,300 A | 5/1991 | Williams |
| 5,034,006 A | 7/1991 | Hosoda et al. |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,195,977 A | 3/1993 | Pollitt |
| 5,215,522 A | 6/1993 | Page et al. |
| 5,232,453 A | 8/1993 | Plass et al. |
| 5,260,066 A | 11/1993 | Wood et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,449,347 A | 9/1995 | Preen et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,678,564 A | 10/1997 | Lawrence et al. |
| 5,735,833 A | 4/1998 | Olson |
| 5,762,640 A | 6/1998 | Kajiwara et al. |
| 5,776,119 A | 7/1998 | Bilbo et al. |
| 5,827,246 A | 10/1998 | Bowen |
| 5,941,859 A | 8/1999 | Lerman |
| 6,071,267 A | 6/2000 | Zamierowski |
| 6,080,243 A | 6/2000 | Insley et al. |
| 6,135,116 A | 10/2000 | Vogel et al. |
| 6,142,982 A | 11/2000 | Hunt et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,458,109 B1 | 10/2002 | Henley |
| 6,471,982 B1 | 10/2002 | Lydon et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,572,594 B2 | 6/2003 | Satterfield et al. |
| 6,660,484 B2 | 12/2003 | Charych et al. |
| 6,682,506 B1 | 1/2004 | Navarro |
| 6,814,079 B2 | 11/2004 | Heaton et al. |
| 7,117,869 B2 | 10/2006 | Heaton et al. |
| 7,195,624 B2 | 3/2007 | Lockwood et al. |
| 7,273,054 B2 | 9/2007 | Heaton et al. |
| 7,276,051 B1 | 10/2007 | Henley et al. |
| 7,316,672 B1 | 1/2008 | Hunt |
| 7,344,512 B2 | 3/2008 | Yamazaki et al. |
| 7,396,339 B2 | 7/2008 | Britto et al. |
| 7,651,484 B2 | 1/2010 | Heaton et al. |
| 7,670,323 B2 | 3/2010 | Hunt et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0127836 A1 | 7/2004 | Sigurjonsson et al. |
| 2005/0261642 A1 | 11/2005 | Weston |

| | | |
|---|---|---|
| 2005/0283105 A1 | 12/2005 | Heaton et al. |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 39 07 007 | 9/1990 |
| DE | 43 06 478 A1 | 9/1994 |
| DE | 295 04 378 U1 | 10/1995 |
| EP | 0 080 179 A1 | 11/1982 |
| EP | 0100148 A1 | 2/1984 |
| EP | 0117632 A2 | 9/1984 |
| EP | 0161865 A2 | 11/1985 |
| EP | 0 300 621 | 1/1989 |
| EP | 0358302 A2 | 3/1990 |
| EP | 0 619 105 A1 | 4/1994 |
| EP | 1018967 B1 | 8/2004 |
| GB | 692578 | 6/1953 |
| GB | 1 579 860 | 4/1976 |
| GB | 2 125 296 A | 3/1984 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 227 035 A | 10/1994 |
| GB | 2 333 965 A | 8/1999 |
| GB | 2 329 127 B | 8/2000 |
| JP | 56-500360 | 3/1981 |
| JP | A-59-141943 | 8/1984 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 90/11795 | 10/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 01/34223 | 5/2001 |
| WO | WO 01/37922 | 5/2001 |
| WO | WO 01/85248 | 11/2001 |
| WO | WO 01/89431 | 11/2001 |
| WO | WO 03/045492 | 6/2003 |
| WO | WO 03/057070 | 7/2003 |

OTHER PUBLICATIONS

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Dukić, Ž. Maksimović, D. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

International Search Report and Written Opinion for International Application No. PCT/US2008/63305; date mailed Aug. 4, 2008.

Notice of Allowance and Fee(s) Due dated May 21, 2001 for U.S. Appl. No. 09/350,581.

Non-Final Office Action dated Jul. 3, 2002 for U.S. Appl. No. 09/835,500.

Response filed Oct. 21, 2002 to Non-Final Office Action dated Jul. 3, 2002 for U.S. Appl. No. 09/835,500.

Notice of Allowance and Fee(s) Due dated Nov. 18, 2002 for U.S. Appl. No. 09/835,500.

Non-Final Office Action dated Mar. 29, 2004 for U.S. Appl. No. 10/366,227.

Response filed May 14, 2005 to Non-Final Office Action dated Mar. 29, 2004 for U.S. Appl. No. 10/366,227.

Notice of Allowance and Fee(s) Due dated Jul. 6, 2004 for U.S. Appl. No. 10/366,227.

Non-Final Office Action dated Dec. 14, 2005 for U.S. Appl. No. 10/937,680.

Response filed Mar. 14, 2006 to Non-Final Office Action dated Dec. 14, 2005 for U.S. Appl. No. 10/937,680.

Notice of Allowance and Fee(s) Due dated Jun. 5, 2006 for U.S. Appl. No. 10/937,680.

Non-Final Office Action dated Sep. 27, 2006 for U.S. Appl. No. 10/983,847.

Response filed Dec. 27, 2006 to Non-Final Office Action dated Sep. 27, 2006 for U.S. Appl. No. 10/983,847.

Final Office Action dated Mar. 22, 2007 for U.S. Appl. No. 10/983,847.

Response filed Apr. 10, 2007 to Final Office Action dated Mar. 22, 2007 for U.S. Appl. No. 10/983,847.

Notice of Allowance and Fee(s) Due dated May 24, 2007 for U.S. Appl. No. 10/983,847.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

Non-Final Office Action dated Jun. 12, 2008 for U.S. Appl. No. 11/702,822.

Response filed Jul. 14, 2008 to Non-Final Office Action dated Jun. 12, 2008 for U.S. Appl. No. 11/702,822.

Non-Final Office Action dated Aug. 26, 2008 for U.S. Appl. No. 11/702,822.

Response filed Nov. 13, 2008 to Non-Final Office Action dated Aug. 26, 2008 for U.S. Appl. No. 11/702,822.

Notice of Allowance dated Apr. 16, 2009 for U.S. Appl. No. 11/702,822.

RCE filed Jun. 4, 2009 for U.S. Appl. No. 11/702,822.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Quayle Office Action dated Nov. 16, 2001 for U.S. Appl. No. 09/613,497.

Response filed Mar. 19, 2004 to Quayle Office Action dated Nov. 16, 2001 for U.S. Application No. 09/613,497.

Non-Final Office Action dated Jul. 13, 2004 for U.S. Application No. 09/613,497.

Response filed Jan. 12, 2005 to Non-Final Office Action dated Jul. 13, 2004 for U.S. Application No. 09/613,497.

Non-Final Office Action dated Feb. 7, 2006 for U.S. Application No. 09/613,497.

Response filed Jul. 8, 2006 to Non-Final Office Action dated Feb. 7, 2006 for U.S. Appl. No. 09/613,497.

Notice of Non-Compliant dated Jul. 14, 2006 for U.S. Application No. 09/613,497.

Response filed Aug. 10, 2006 to Non-Compliant dated Jul. 14, 2006 for U.S. Appl. No. 09/613,497.

Notice of Allowance and Fee(s) Due dated Oct. 13, 2006 for U.S. Appl. No. 09/613,497.

Request for Continued Examination dated Feb. 26, 2007 for U.S. Appl. No. 09/613,497.

Notice of Allowance and Fee(s) Due dated Apr. 5, 2007 for U.S. Appl. No. 09/613,497.

Request for Continued Examination dated Jul. 9, 2007 for U.S. Appl. No. 09/613,497.

Response filed Jul. 19, 2007 to Interview Summary dated Jul. 19, 2007 for U.S. Appl. No. 09/613,497.

Notice of Allowance dated Aug. 6, 2007 for U.S. Appl. No. 09/613,497.

Non-Final Office Action dated Oct. 18, 2007 for U.S. Appl. No. 11/713,485.

Response filed Mar. 18, 2008 to Non-Final Office Action dated Oct. 18, 2007 for U.S. Appl. No. 11/713,485.

Non-Final Office Action dated Jun. 26, 2008 for U.S. Appl. No. 11/713,485.

Response filed Sep. 8, 2008 to Non-Final Office Action dated Jun. 26, 2008 for U.S. Appl. No. 11/713,485.

Non-Final Office Action date mailed Dec. 10, 2008 for U.S. Appl. No. 11/713,485.

Response filed Mar. 4, 2009 for U.S. Appl. No. 11/713,485.

Final Office Action date mailed May 19, 2009 for U.S. Appl. No. 11/713,485.

Interview Summary date mailed Jul. 17, 2009 for U.S. Appl. No. 11/713,485.

RCE/Response filed Aug. 21, 2009 for U.S. Appl. No. 11/713,485.

Notice of Allowance date mailed Nov. 30, 2009 for U.S. Appl. No. 11/713,485.

Notice of Allowance dated Aug. 24, 2009 for U.S. Appl. No. 11/702,822.

Notice of Allowance dated Sep. 14, 2009 for U.S. Appl. No. 11/702,822.

Notice of Allowance dated Dec. 3, 2009 for U.S. Appl. No. 11/702,822.

Notice of Opposition date mailed Apr. 28, 2010 in European Patent No. 1772160.

Notice of Opposition date mailed Oct. 13, 2010 to European Patent No. 1637088.

Teder, et al., "Continuous Wound Irrigation in the Pig," Journal of Investigative Surgery, vol. 3, pp. 399-407; 1990.

Restriction Requirement date mailed Sep. 27, 2010 for U.S. Appl. No. 12/118,524.

Response filed Oct. 20, 2010 for U.S. Appl. No. 12/118,524.

SURGICAL DRAPE AND SUCTION HEAD FOR WOUND TREATMENT

CROSS-REFERENCE TO RELATED APPLICATION

This application is a continuation of copending U.S. application Ser. No. 10/937,680, filed Sep. 9, 2004, which is a continuation of U.S. application Ser. No. 10/366,227, filed on Feb. 13, 2003, which is a continuation of U.S. application Ser. No. 09/835,500, filed on Apr. 16, 2001, now U.S. Pat. No. 6,553,998, which is a continuation of Ser. No. 09/350,581, filed on Jul. 9, 1999, now U.S. Pat. No. 6,345,623, which is a continuation, under 35 U.S.C. §120 of PCT international application number PCT/GB98/02713 filed Sep. 9, 1998 and designating the United States, which claims priority to Great Britain patent application No. 9719520.0 filed Sep. 12, 1997. By this reference, the full disclosure of U.S. application Ser. No. 09/350,581, PCT international application No. PCT/GB98/02713, and Great Britain patent application No. 9719520.0 are incorporated herein as though fully set forth in their respective entirety.

BACKGROUND OF THE INVENTION

1. Field of the Invention

This invention relates to surgical drapes and suction heads for wound treatment.

2. Description of the Related Art

Surgical drapes are widely used in surgical operations for the purpose of reducing infection and facilitating the handling of skin around incisions. Normally, they are transparent or translucent. Typically, they consist of a flexible, plastic film which is adhesive-coated and which is applied to the area of the operation, prior to making the incision. Surgical drapes are also used for attaching treatment devices to patients after an operation, such as catheters or drainage tubes.

A further, recently developed use is for connecting a suction tube to a wound for the purpose of stimulating healing of the wound. Such use is described in our earlier applications Nos. WO 96/05873 and WO 97/18007.

Various proposals have been made in the past to design the surgical drape so that handling of the sticky, flexible, plastic film is facilitated. For example, U.S. Pat. No. 5,437,622 describes a surgical drape which is a laminate of three materials. The first material comprises a transparent, thin plastic film which is adhesive-coated and the adhesive face protected with a layer of release-coated paper. The other face of the adhesive-coated film is strengthened with a reinforcing layer of a less flexible, plastic film. Handling bars or strips are attached to the flexible, plastic film at its lateral edge to facilitate handling of the flexible, plastic film after stripping away the protective releasable layer.

Where is it is desirable to use a surgical drape primarily to attach a device such a s a catheter to a wound area after an operation or for long term treatment, it is inconvenient for the surgeon or nurse to have to adapt a standard surgical drape for this purpose. It would be more convenient to have a surgical drape which was suitable without adaptation to accommodate the treatment device.

SUMMARY OF THE INVENTION

One aspect of the present invention is directed to a solution to this problem. A second aspect provides a combined surgical drape and suction head for applying suction to a wound area to facilitate application of negative pressure therapy.

According to one aspect of the present invention there is provided a surgical drape which comprises a thin, flexible, adhesive-coated plastic film and a strengthening layer applied to the face opposite to the adhesive coating, the strengthening layer being a plastic film which is thicker or less flexible than said adhesive-coated film, and a protective, releasable layer applied to the adhesive coating, the drape having an aperture through at least the strengthening and adhesive coated film to permit, in use, access to a wound area, a first edge of the drape having non-adhesive coated handling bars for separating the adhesive-coated film from the protective layer, and wherein the protective layer comprises a separate strip extending parallel to the first edge of the drape, and which protects the adhesive coating in the region of the aperture and carries a flap overlapping the adjacent portion of the protective layer, said flap constituting a handle for facilitating removal of said strip prior to use. Preferably, non-adhesive coated handling bars are positioned at opposite lateral edges of the drape.

In practice, surgical drapes may be manufactured by laminating an adhesive-coated flexible film, such as a polyurethane film, to a protective releasable layer, such as a siliconized paper. A strengthening layer of thicker plastic material, e.g. a polyolefin such a polyethylene, may be applied to the non-adhesive coated face of the flexible film, so that a three-layer laminate is produced. These laminates are produced in substantial width and may be slit longitudinally to the desired width and then laterally to form drapes of the desired size.

After slitting to a desired width, handling bars are normally applied to the adhesive-coated layers at one or both lateral edges to facilitate separation of the film from the protective, releasable layer. While an aperture could be cut at the desired position through the layers to accommodate a catheter or a device such as those described in our above-mentioned applications, it is difficult to handle the highly pliable and adhesive film after the releasable layer has been stripped off.

Although the strengthening layer does somewhat improve the handling characteristics, this is not a complete answer to the problem. However, the handling characteristics are substantially improved by providing a protective layer which is in at least two portions, one of which is in the form of a strip, e.g. one extending parallel to the lateral edges of the drape, and covering the peripheral area around the aperture through the drape. By providing a flap on this portion of the releasable layer, it can be stripped off initially so that the drape is first positioned around the device which is to pass through the aperture, and then the remaining part of the protective releasable layer is stripped off to adhere the drape to the patient's skin around the area to be treated.

In a preferred form of the invention in which negative pressure therapy is applied to a wound area, the surgical drape described above is combined with a suction head having a connector piece which is adapted to be connected to a suction tube. Thus, in this embodiment, the suction head can be adhered to the patient's skin in the area of the wound after removing the strip of protective releasable layer, and then the remaining part of the drape affixed to the patient's skin. In this way, the suction head is held firmly in place and, at the same time, seals the suction head to the wound area and prevents leakage of air from atmosphere into the wound area.

The invention also includes a suction head having a design which facilitates the suction of fluid from a wound area.

According to a further feature of the invention, therefore, there is provided a suction head for applying suction to a wound area which comprises a generally planar flange portion and a tubular connector piece on a first face, for connecting a suction tube to an aperture through the flange portion to the other face, said other face having projections defining flow channels facilitating flow of fluid towards said aperture.

Preferably, the suction head described above is combined with a surgical drape, the drape comprising a thin, flexible, adhesive-coated plastic film, and the tubular connector piece extends through an opening in the plastic film with the adhesive coating adhered to said first face of the flange portion.

Preferably, the suction head is used in conjunction with an open-celled foam pad so that one surface of the foam pad is placed in contact with a wound area and the suction head applied to the other surface of the foam pad. In the case of deep wounds the foam may be shaped and placed so that it is packed into the wound cavity as described in our above-cited PCT applications. According to another technique, which is particularly applicable to superficial wounds, the foam pad may be a relatively thin pad which is placed over the wound. The suction head is placed in contact with the open face of the foam pad and the drape applied over the suction head to fix the assembly to the patient's skin.

Various types of open celled foams can be used as described in our above-cited PCT applications. The foam may be a polyurethane foam but polyvinyl acetate (PVA) foams are preferred, especially when used as a pad which placed over the wound. These are to some extent hydrophilic, which seems to exhibit beneficial comfort properties when applied to the skin. Wound healing is stimulated by maintenance of moist conditions in the wound area, and this is facilitated by using a hydrophilic foam.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DESCRIPTION OF THE PREFERRED EMBODIMENTS

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 1:
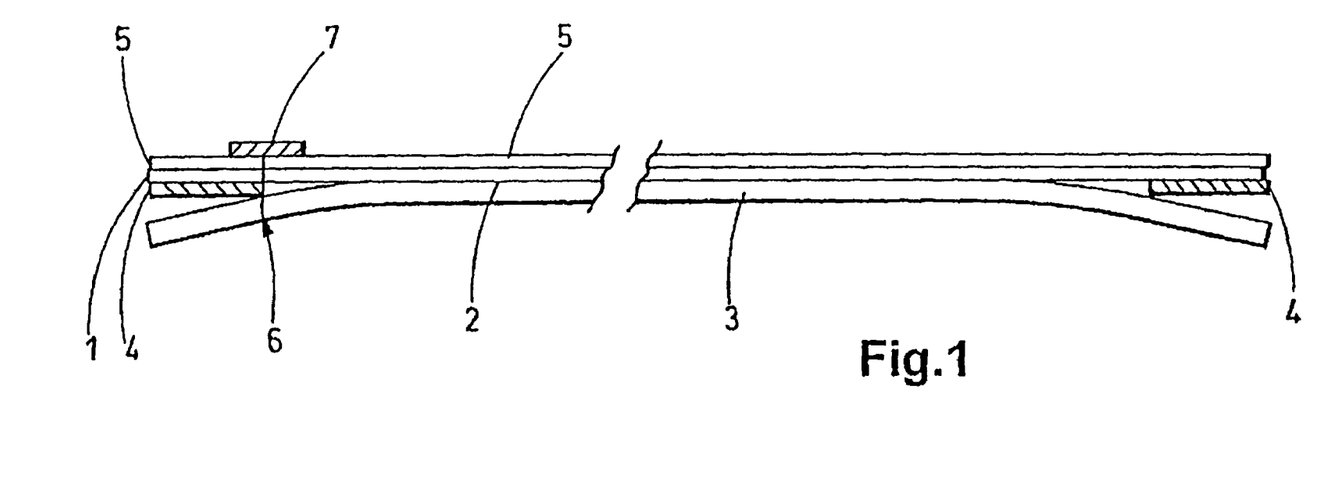
FIG. 1 represents a conventional design of surgical drape.
Figure 2:
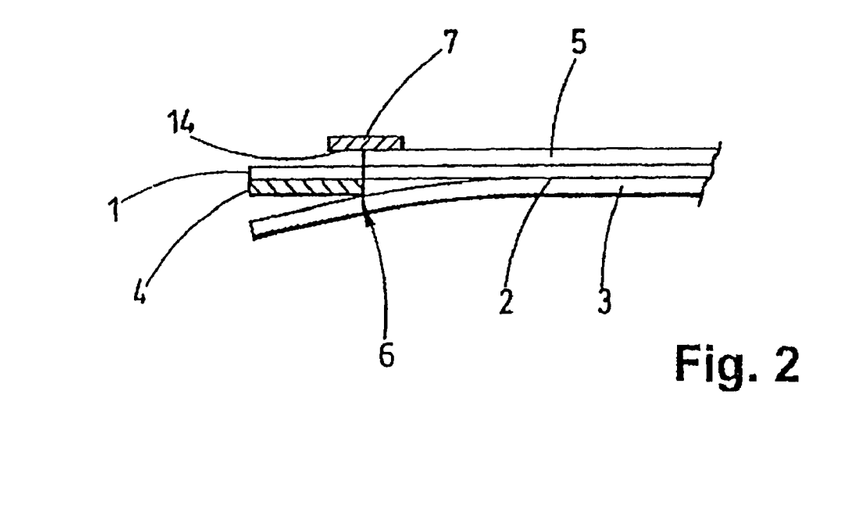
FIG. 2 represents a variation in the design of the handling bars at one end of the drape shown in FIG. 1.

Referring to FIGS. 1 and 2 of the accompanying drawings, a conventional laminate for use as a surgical drape comprises a thin, flexible, transparent film 1 which is adhesive-coated on one face 2, normally with a high-tack pressure-sensitive adhesive, and is protected with a releasable layer 3. The thin plastic film is conveniently of polyurethane because is transmits moisture. Layer 3 is normally considerably thicker than film 1 and is coated on the surface adjacent to the adhesive with a releasable material such as a silicone to facilitate stripping away from the adhesive-coated film.

In order to facilitate removal of the adhesive-coated film prior to use of the device, handling bars 4 are bonded at each end to the adhesive-coated film 1. Thus, by holding one of the bars 4, the protective layer 3 can be stripped off and the adhesive face applied to the skin of the patient. To facilitate handling of the thin, flexible film 1, a strengthening plastic film 5 is frequently applied to the free face of the plastic film 1. This is generally also transparent or translucent. Film 5 is preferably not bonded with adhesive to film 1, but may remain, in contact by reason of electrostatic forces or because of close contact between the two conforming surfaces of film 1 and film 5.

Usually, the surgeon or nurse will wish to strip off the protective layer 5 after the film 1 has been correctly placed on the patient's skin, and this can be facilitated by making partial cuts 6 through the film 1 and 5, so that as the handling bar 4 is drawn upwards from the patient's skin, the adhesive film 1 remains adhered to the patient, while the patient, while the partial cuts 6 cause separation of the flexible film from the strengthening film 5. Strengthening bars 7 may be provided to hold the lateral edges of the strengthening film 5 and film 1 together with their main parts.

An alternative arrangement is shown in FIG. 2, in which the strengthening film 5 is provided with a separate overlapping handling bar 14, to facilitate its removal from the flexible film 1.

Further details of the make-up and manufacture of surgical drapes are given in U.S. Pat. No. 5,437,622 and European patent application no. 0161865 and the prior art referred to therein, by this reference, the full disclosure of U.S. Pat. No. 5,437,622 and European patent application no. 0161865 are incorporated herein as though each now set forth in its respective entirety.

Figure 3:
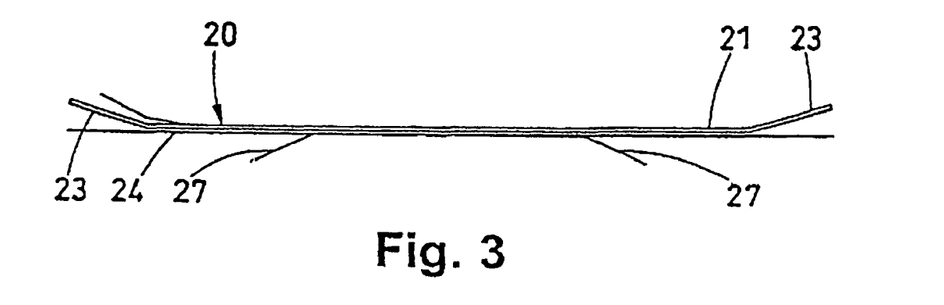
FIG. 3 is a view similar to FIG. 1 of a surgical drape in accordance with the invention.
Figure 4:
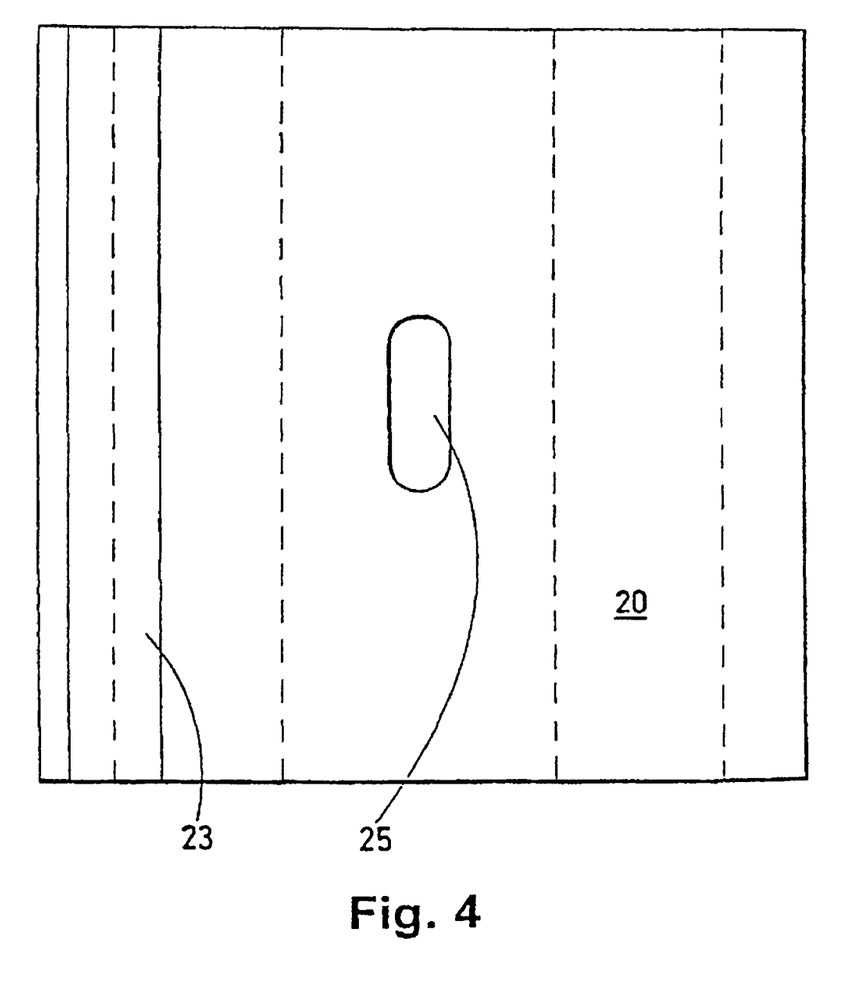
FIG. 4 is a plan view of the surgical drape shown in FIG. 3.

Referring to FIGS. 3 and 4, the surgical drape of the present invention comprises a protective outer film 20, laminated to a thin, flexible film 21. The flexible film includes an adhesive-coated layer which is protected with a release-coated sheet material 24. Lateral edges of the flexible film 21 are provided with handling bars 23. Thus far, the design is essentially the same as that shown in FIGS. 1 and 2.

The drape of the present invention differs from the drape shown in FIGS. 1 and 2 in that an aperture 25 is but through the strengthening layer 20 and through the flexible layer 21. The other difference compared with the prior art drapes is that the protective releasable layer is formed in at least two sections.

In the embodiments shown in FIGS. 3 and 4, the central portion of the releasable layer comprises a strip 26, having flaps 27 which overlap the remaining outboard portions of the releasable layer. The purpose of this is to enable the central strip 26 to be removed first, without disturbing the remaining portions of the releasable layer. The drape can then be fitted around the wound area and, if desired, a suction device or other treatment device passed through the aperture 25 and secured to the patient's skin with the peripheral areas of exposed adhesive coated film.

Figure 5:
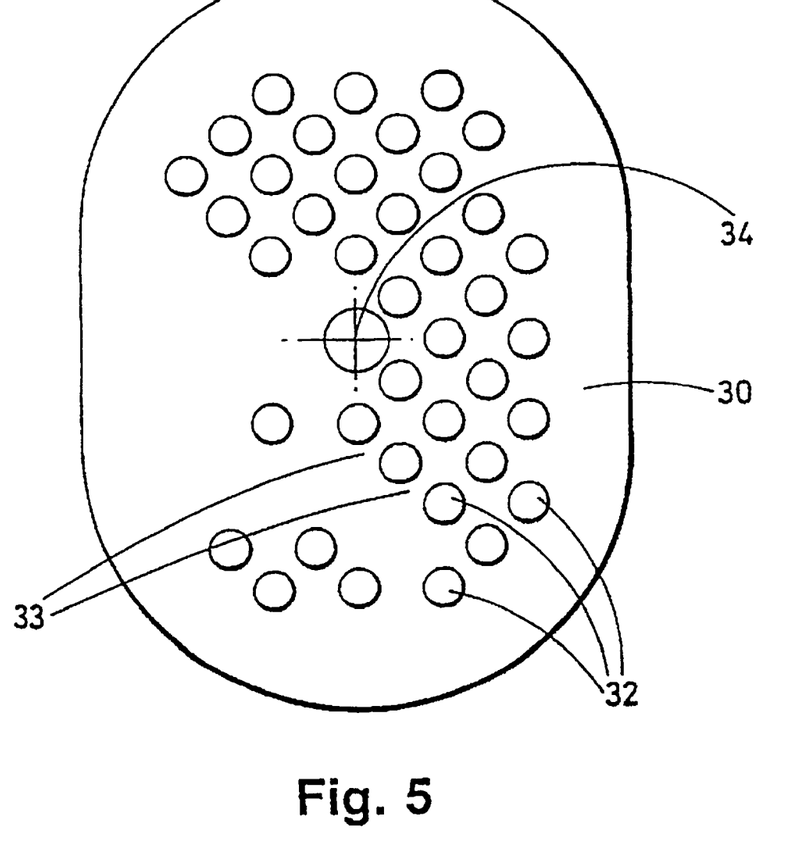
FIG. 5 is a plan view from beneath of a suction head in accordance with the invention.
Figure 6:
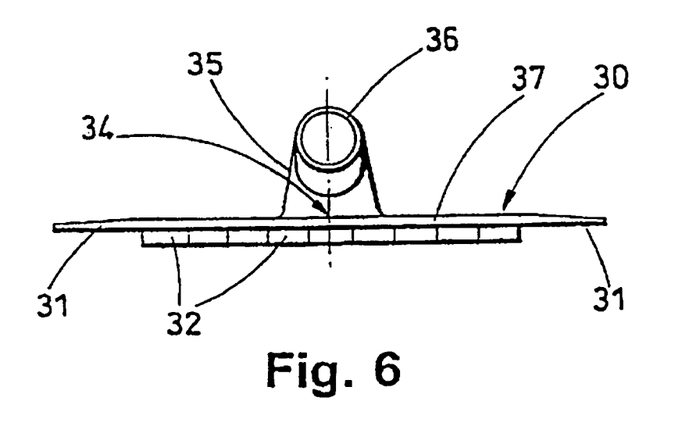
FIG. 6 is a side elevation of the suction head shown in FIG. 5.
Figure 7:
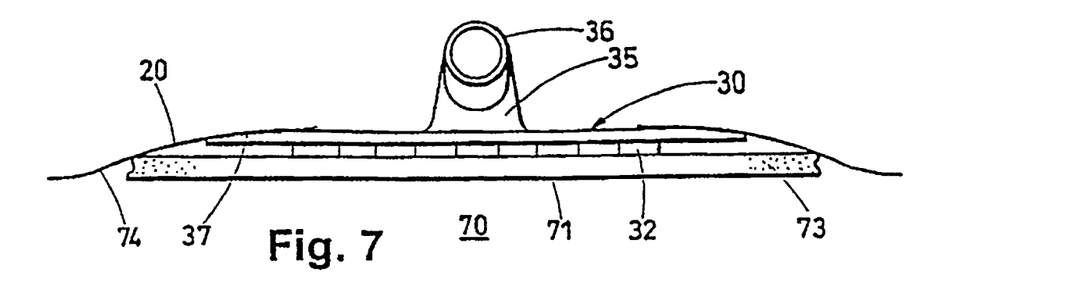
FIG. 7 is a view similar to FIG. 6 but shows the suction head secured to a skin surface with the drape and with a foam pad located between the head and the skin surface.

An example of a device for applying suction to the wound area is illustrated in FIGS. 5, 6, and 7.

Referring to these figures, the suction head comprises a flange portion 30 having a tapered edge 31, and a profile which may be of any desired shape but is generally rounded at its edges. On the face of the flange 30 intended for contact with the patient's skin or a foam pad are formed a series of projections 32 which are distributed over the surface of the flange apart from the peripheral edge portion 31. The purpose of these projections is to provide fluid channels 33 facilitating the flow of fluids form any point of the flange to a central point 34, from which it is intended to apply suction. The suction head includes a connector 35, located above the aperture 34, having a tubular end 36 adapted for receiving and connecting a catheter. The tubular and may have an outwardly tapered portion to facilitate feeding a catheter into the connector. The upper surface 37 of the suction head has a substantially smooth surface.

In use, the connector portion 35 is sized so that it extends through the aperture 25 in the surgical drape shown in FIGS. 3 and 4, with the adhesive surface around the aperture bonded to the smooth surface 37 of the flange 30. The suction head may be packaged in this condition with the surgical drape so that in use, the strip 26 is removed by pulling on the handles 27 thus exposing the adhesive surface in the vicinity of and surrounding the suction head. The suction head can then be fixed in the desired position on the patient's wound and then the remaining portion of the protective film removed to fix the drape to the patient. The flange 30 of the suction head may be somewhat oval as shown in FIG. 5, and have dimensions as indicated in this Figure i.e. a longer dimension of about 95 mm and short dimension of about 70 mm. Alternatively, the flange may be circular and be smaller in plan view. For example, the diameter of a circular suction head may be from about 30 to 50 mm in diameter, e.g. about 40 mm. It has been found that the suction head flange should not overlap the area of the wound. Thus, in the case of smaller wounds a smaller head is indicated.

FIG. 7 shows the suction head attached to a wound area 71 of a patient 70. The suction head is pressed into firm contact with a flexible, open-celled foam 73, which is itself pressed into contact with a wound area 71. The suction head and foam pad are pressed into contact with the wound area by a surgical drape 20 having an adhesive surface 74. The adhesive surface is bonded to the patient's skin outside the periphery of the foam pad and suction head. It is also bonded to upper surface 37 of the suction head. An aperture is formed in the drape to permit the connector portion 35 to extend upwardly through the drape. In order to avert the danger of incorrect catheter tubes being fitted to the connector 35, the latter may have a customized cross-section or internal projection such as a rib or key which cooperates with a corresponding slot, or key way in the catheter. Alternatively, the catheter may be molded with a projection or longitudinal rib which operates with a corresponding slot or key way in the aperture of the connector 35.

The foam pad may be packaged in a plastic pouch, sterilized by gamma irradiation and supplied in the same box or in other packing units as the suction head and drape.

Figure 8:
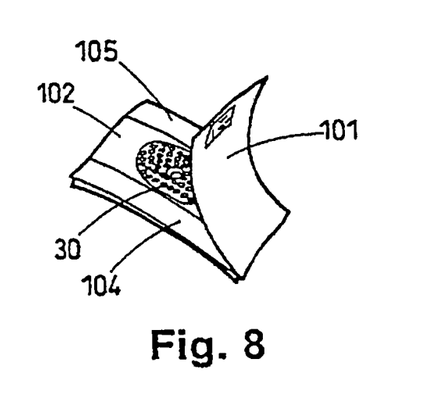
FIG. 8 is a perspective view of the drape with a central strip portion of the protective sheet in the course of being removed.
Figure 9A:
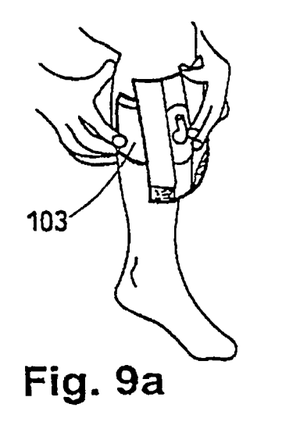
FIGS. 9a through 9c illustrate the steps of affixing the dressing assembly to a wound area on a patient's leg and attachment to a negative pressure assembly.
Figure 9B:
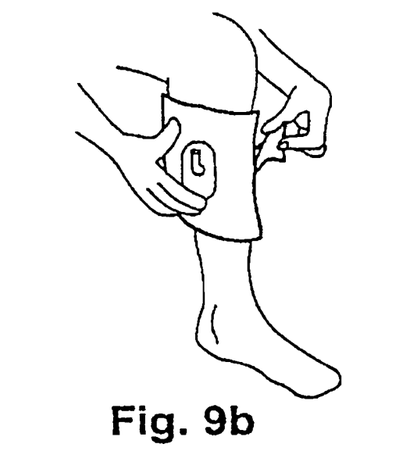
Figure 9C:
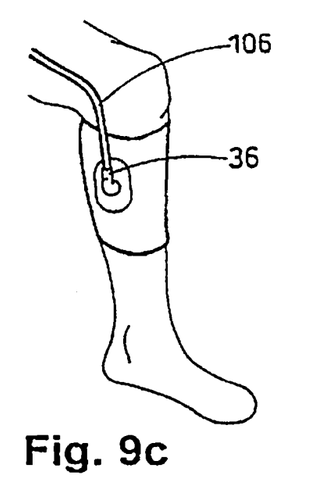

FIGS. 8, 9a, and 9b illustrate the way in which the drape-suction head combination is fitted to a wound on the patient's skin. In FIG. 8, a backing sheet 101 having a release coated surface is removed in the first step from the adhesive face 102 of the drape to expose the face of connector 30. A pad 103 of foam is positioned over the wound area and the drape placed over the foam pad, the drape being adhered to the skin above and below the pad (FIG. 9a). The lateral protective strips 104 and 105 are removed in turn from the drape and the assembly adhered to the skin (FIGS. 9b and 9c). Finally, spout 36 is connected to a tube 106 which is then connected to a source of suction, e.g. a pump as described in our above PCT application, in order to apply negative pressure to the wound. The suction head and drape assembly as shown in FIG. 8, with the smooth surface 37 adhered to the drape, is conveniently packaged in an easily openable plastic bag or pouch, and sterilized for immediate use.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. In any case, because the scope of the present invention is much broader than any particular embodiment, the foregoing detailed description should not be construed as a limitation of the scope of the present invention, which limited only by the claims appended hereto.

We claim:

1. A wound therapy combination comprising:
   a suction head having a flange portion and a connector adapted to be connected to a suction tube; and
   a drape to secure the suction head at a wound site of a patient, the drape having an adhesive-coated film, a first releasable protective layer, and a second releasable protective layer, the first releasable protective layer covering a first portion of the adhesive-coated film that is adapted to be adhered to the flange portion of the suction head, the second releasable protective layer covering a second portion of the adhesive-coated film adapted to be adhered to skin of the patient.

2. The wound therapy combination of claim 1 further comprising:
   a foam pad adapted to be positioned in contact with the wound site;
   wherein the suction head is adapted to be positioned in contact with the foam pad.

3. The wound therapy combination of claim 2, wherein the foam pad is an open-celled polymer foam pad.

4. The wound therapy combination of claim 2, wherein the foam pad is hydrophilic.

5. The wound therapy combination of claim 1, wherein the suction head is positionable in contact with the wound site.

6. The wound therapy combination of claim 1, wherein the first portion of the adhesive-coated film is a central portion of the adhesive-coated film.

7. The wound therapy combination of claim 1 further comprising:
   an aperture in the adhesive-coated film to receive the connector of the suction head.

8. The wound therapy combination of claim 1 further comprising:
   an aperture in the adhesive-coated film to receive the connector of the suction head;
   wherein the first portion of the adhesive-coated film is a central portion; and
   wherein the central portion surrounds the aperture.

9. The wound therapy combination of claim 1, wherein the first releasable protective layer further comprises:
   a flap overlapping the second releasable protective layer.

10. The wound therapy combination of claim 1, wherein the drape further comprises:

a strengthening film that is less flexible than the adhesive-coated film.

11. The wound therapy combination of claim 10, wherein the strengthening film is separable from the adhesive-coated film.

12. The wound therapy combination of claim 1, wherein the flange portion of the suction head includes a tapered edge.

13. A wound therapy combination comprising:
- a suction head having a first face, a second face opposite the first face and an opening between the first face and the second face, the opening being adapted for connection to a suction tube;
- a surgical drape having an aperture coincident the opening, the surgical drape extending over the first face of the suction head and extending beyond a perimeter of the first face; and
- wherein the surgical drape comprises a flexible adhesive-coated film adhered to the first face and a release-coated backing covering a portion of the adhesive-coated film that extends beyond the perimeter of the first face.

14. The wound therapy combination of claim 13 further comprising:
- a foam pad adapted to be positioned in contact with the suction head.

15. The wound therapy combination of claim 14, wherein the foam pad is an open-celled polymer foam pad.

16. The wound therapy combination of claim 14, wherein the foam pad is hydrophilic.

17. The wound therapy combination of claim 13, wherein the suction head is positionable in contact with a wound site.

18. The wound therapy combination of claim 13, wherein the surgical drape further comprises:
- a strengthening film that is less flexible than the adhesive-coated film.

19. The wound therapy combination of claim 18, wherein the strengthening film is separable from the adhesive-coated film.

20. The wound therapy combination of claim 13, wherein the suction head further comprises:
- a flange portion; and
- a connector.

21. The wound therapy combination of claim 20, wherein the flange portion of the suction head includes a tapered edge.

* * * * *